(12) United States Patent  
Kim et al.

(10) Patent No.: US 7,910,934 B2
(45) Date of Patent: Mar. 22, 2011

(54) SELF-ASSEMBLED HETEROGENEOUS INTEGRATED OPTICAL ANALYSIS SYSTEM

(75) Inventors: Samuel Kim, Austin, TX (US); Babak Amirparviz, Seattle, WA (US); Deirdre Meldrum, Phoenix, AZ (US); Ehsan Saeedi, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 12/497,518

(22) Filed: Jul. 2, 2009

(65) Prior Publication Data

US 2010/0096640 A1     Apr. 22, 2010

Related U.S. Application Data

(63) Continuation of application No. PCT/US2008/050104, filed on Jan. 3, 2008.

(60) Provisional application No. 60/883,696, filed on Jan. 5, 2007.

(51) Int. Cl.
*H01L 27/15*     (2006.01)
*H01L 29/16*     (2006.01)
*H01L 31/12*     (2006.01)
*H01L 33/00*     (2006.01)

(52) U.S. Cl. ............... 257/82; 257/80; 257/81; 257/84; 257/88; 438/26; 438/116

(58) Field of Classification Search ............. 257/80–82, 257/84, 88; 438/26, 116
See application file for complete search history.

(56) References Cited

U.S. PATENT DOCUMENTS

| 5,824,186 | A | 10/1998 | Smith |
| 5,904,545 | A | 5/1999 | Smith |
| 6,623,579 | B1 | 9/2003 | Smith |
| 6,687,987 | B2 | 2/2004 | Mayer |
| 6,731,353 | B1 | 5/2004 | Credelle |
| 6,780,696 | B1 | 8/2004 | Schatz |
| 6,790,692 | B2 | 9/2004 | Onozawa |
| 6,982,819 | B2 | 1/2006 | Sawin |
| 7,007,370 | B2 | 3/2006 | Gracias |
| 7,018,867 | B2 | 3/2006 | Gracias |
| 7,157,741 | B2 | 1/2007 | Kim |
| 7,625,780 | B2 | 12/2009 | Jacobs |
| 7,629,026 | B2 | 12/2009 | Sharma |
| 2006/0052293 | A1 | 3/2006 | Climent-Johansson |
| 2006/0261432 | A1 | 11/2006 | Yoshimura |
| 2007/0215273 | A1 | 9/2007 | Jacobs |
| 2009/0230174 | A1 | 9/2009 | Kim |

FOREIGN PATENT DOCUMENTS

| WO | 2007/150066 A1 | 12/2007 |
| WO | 2008/086090 A1 | 7/2008 |

OTHER PUBLICATIONS

Böhringer, K.F., et al., "Modeling of Capillary Forces and Binding Sites for Fluidic Self-Assembly," Proceedings of the 14th IEEE International Conference on Micro Electro Mechanical Systems [MEMS 2001], Interlaken, Switzerland, Jan. 21-25, 2001, pp. 369-374.

*Primary Examiner* — Zandra Smith
*Assistant Examiner* — Telly D Green
(74) *Attorney, Agent, or Firm* — Christensen O'Connor Johnson Kindness PLLC

(57) ABSTRACT

Optical analysis system fluidically self-assembled using shape-coded freestanding optoelectronic components and a template having shape-coded recessed binding sites connected by an embedded interconnect network. Also includes methods of manufacture and use for optical analyses.

21 Claims, 11 Drawing Sheets

US 7,910,934 B2

SELF-ASSEMBLED HETEROGENEOUS INTEGRATED OPTICAL ANALYSIS SYSTEM

CROSS-REFERENCE TO RELATED APPLICATION

This application is a continuation of International Application No. PCT/U.S. 2008/050104, filed Jan. 3, 2008, which claims the benefit of U.S. Provisional Application No. 60/883,696, filed Jan. 5, 2007, each application is incorporated herein by reference in its entirety.

STATEMENT OF GOVERNMENT LICENSE RIGHTS

This invention was made with Government support under Government Contract Nos. 2R01 HG01497 and 5 P50 GH002360 awarded by the National Institutes of Health. The Government has certain rights in the invention.

BACKGROUND OF THE INVENTION

Macroelectronics is an emerging area of interest in the semiconductor industry. Unlike the traditional pursuit in microelectronics to build smaller devices and achieve higher degrees of integration over small areas, macroelectronics aims to construct distributed active systems that cover large areas. Often, these systems are constructed on flexible substrates with multiple types of components and allow for distributed sensing and control. A number of applications are already under consideration for macroelectronics including smart artificial skins, large-area phased-array radars, solar sails, flexible displays, electronic paper and distributed x-ray imagers. A macrofabrication technology should generally be able integrate a large number of various functional components over areas exceeding the size of a typical semiconductor wafer in a cost-effect and time-efficient fashion.

An alternative approach for construction of macroelectronic systems is to perform the integration at the device level instead of the material level. Significant infrastructure is available to cost-effectively fabricate high-performance devices on single-crystal semiconductor substrates. Even though recent advances in robotic assembly allow for positioning of up to 26,000 components per hour on plastic substrates, the relatively moderate speed, high cost, and limited positional accuracy of these systems make them unsuitable candidates for cost-effective mass production of macroelectronics.

A powerful technology that can meet all criteria for an effective macrofabrication technology is self-assembly. In a device-level integration approach based on self-assembly, functional devices are batch microfabricated and released to yield a collection of freestanding components. These components are then allowed to self-assemble onto a template, for example on a plastic substrate, to yield a functional macroelectronic system. Self-assembly, implemented in the fashion outlined above, is an inherently parallel construction method that allows for cost-effective and fast integration of a large number of functional components onto unconventional substrates. For example, it allows for integration of components made from incompatible microfabrication processes (e.g., light-emitting diodes made in compound semiconductor substrates and silicon transistors) onto non-planar flexible substrates. Key components of a self-assembly-based macroelectronic fabrication technology include: (a) development of fabrication processes that generate freestanding micron-scale functional components, (b) implementation of recognition/binding capabilities that guide the components to bind in the correct location, and (c) determination of self-assembly procedures/conditions that construct the final system with a high yield. A fluidic self-assembly method is disclosed in international application No. PCT/U.S. 2007/072038, filed Jun. 25, 2007, which is hereby incorporated by reference.

Self-assembly of micron-scale and millimeter-scale components have been studied previously both for two-dimensional (2D) and three-dimensional (3D) integration. In 2D integration via self-assembly, a template with binding sites is prepared and a collection of parts is allowed to self-assemble onto the proper binding sites. The assembly procedure is performed in a liquid medium to allow for free motion of the components. Capillary forces are used to bind the components to the template and forces resulting from fluid flow and gravity are used to move the components and drive the system toward a minimum energy state. A major drawback of demonstrated self-assembly to this date has been the requirement of post-processing. Historically, further processing of the substrate in a clean-room has been necessary to provide electrical connections and complete the assembly procedure. The need for post-processing has limited the applicability of prior-art fluidic self-assembly methods. Self-assembly has also been used for 3D integration of freestanding millimeter-scale parts or folding of components placed on ribbons into electrical circuits. In order for the full potential of these techniques to be realized, batch microfabrication processes are needed to generate a large number of micron-scale functional components that can participate in self-assembly.

The integration of micro-optical and electronic components on a common substrate has proven to be a challenging task due to the incompatibility of the respective microfabrication processes employed for the different components. Light-emitting substrates required for excitation, such as III-V materials (semiconductor alloys made from elements from Group III and Group V on the periodic table), typically require entirely different fabrication processes than CMOS- or silicon-based manufacturing processes. As a result, current integration strategies require complex fabrication techniques to achieve fully integrated devices. A simplified method for fabricating micro-optical and electronic components on a common substrate is necessary to enable future macroelectronic devices.

SUMMARY OF THE INVENTION

The present invention provides devices for optical analysis, methods for fabricating devices, and methods for optical analysis using the devices.

In one aspect, the invention provides devices for optical analysis. In one embodiment, the device includes a template having a plurality of first recessed binding sites with a first shape and a plurality of second recessed binding sites with a second shape, the template having an embedded interconnect network interconnecting the first and second recessed binding sites, where each of the first and second recessed binding sites contains an attachment means; a plurality of light-emitting components having the first shape and at least two electrodes, received into at least some of the first recessed binding sites and electrically connected to the embedded interconnect network by the attachment means; and a plurality of light-detecting components having the second shape and at least two electrodes, received into at least some of the second recessed binding sites and electrically connected to the embedded interconnect network by the attachment means.

In another aspect, the device includes a first template having a plurality of first recessed binding sites with a first shape, the first template having a first embedded interconnect network interconnecting the first recessed binding sites, where each of the first recessed binding sites contains an attachment means; a plurality of light-emitting components having the first shape and at least two electrodes, received into at least some of the first recessed binding sites and electrically connected to the first embedded interconnect network by the attachment means; a second template having a plurality of second recessed binding sites with a second shape, the second template having a second embedded interconnect network interconnecting the second recessed binding sites, where each of the second recessed binding sites contains an attachment means; and a plurality of light-detecting components having the second shape and at least two electrodes, received into at least some of the second recessed binding sites and electrically connected to the second embedded interconnect network by the attachment means.

In another aspect, methods for making optical analysis devices are provided. In one embodiment, the invention provides a method for fabricating an optical analysis device on a single template. In this embodiment, the method includes fabricating a plurality of freestanding light-emitting components having a first shape and at least two electrodes; fabricating a plurality of freestanding light-detecting components having a second shape and at least two electrodes; fabricating a template having: i) an embedded interconnect network, ii) a plurality of first recessed binding sites shaped to receive the light-emitting components, and iii) a plurality of second recessed binding sites shaped to receive the light-detecting components; providing an attachment means in the first and second recessed binding sites; immersing the template in a liquid; introducing the plurality of freestanding light-emitting components and the plurality of freestanding light-detecting components into the liquid such that at least some of the light-emitting components are received into at least some of the first recessed binding sites and at least some of the light-detecting components are received into at least some of the second recessed binding sites, such that the received light-emitting components and the received light-detecting components are electrically connected to the embedded interconnect network by the attachment means.

In another aspect, the invention provides a method for fabricating an optical analysis device having two templates. In this embodiment, the method includes fabricating a plurality of freestanding light-emitting components having a first shape and at least two electrodes; fabricating a first template having a first embedded interconnect network and a plurality of first recessed binding sites shaped to receive the light-emitting components, where the first recessed binding sites contains an attachment means that is electrically connected to the first embedded interconnect network; immersing the first template in a first liquid; introducing the plurality of freestanding light-emitting components into the first liquid such that at least some of the light-emitting components are received into at least some of the first recessed binding sites such that the received light-emitting component are electrically connected to the embedded interconnect network by the attachment means; fabricating a plurality of freestanding light-detecting components having a second shape and at least two electrodes; fabricating a second template having a plurality of second recessed binding sites shaped to receive the light-detecting components, where the second recessed binding sites contains an attachment means that is electrically connected to a second embedded interconnect network; immersing the second template in a second liquid; introducing the plurality of freestanding light-detecting components into the second liquid such that at least some of the light-detecting components are received into at least some of the second recessed binding sites such that the received light-detecting components are electrically connected to the embedded interconnect network by the attachment means.

In another aspect, the invention provides a method for performing optical analysis using devices of the invention. In one embodiment, the method includes fluidically self-assembling a plurality of freestanding light-emitting components having a first shape and a plurality of freestanding light-detecting components having a second shape on a template having an embedded interconnect network using component-specific shaped recesses in the template, where the components are connected to the embedded interconnect network by an attachment means; positioning the template such that the light-emitting components and the light-detecting components are in optical communication with an analyte; activating the light-emitting components such that light emitted from the light-emitting component produces an optical response in the analyte; and detecting the optical response with the light-detecting components.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

Figure 1A:
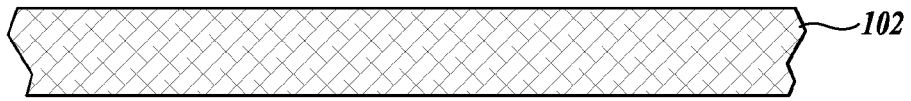
FIGS. 1A-1G illustrate the fabrication of a representative device in accordance with the present invention.

The present invention provides devices for optical analysis, methods for fabricating devices, and methods for optical analysis using the devices. A method is disclosed for the self-assembly of shape-coded optoelectronic (OE) components into a template having shape-coded recesses that provide access to an embedded interconnect network. The OE components are received into the shape-coded recesses and are electrically connected to the embedded interconnect network with an attachment means. The self-assembly takes place in a liquid bath containing the shape-coded template and freestanding OE components shape-coded to fit into the recesses of template. A representative device includes light-emitting components (LECs) and light-detecting components (LDCs) assembled onto a template. An optical analysis system is completed by introducing an analyte that is in optical communication with the OE components, typically via a channel or well-plate.

In one aspect, the invention provides devices for optical analysis. In one embodiment, the device includes a template having a plurality of first recessed binding sites with a first shape and a plurality of second recessed binding sites with a second shape, the template having an embedded interconnect network interconnecting the first and second recessed binding sites, where each of the first and second recessed binding sites contains an attachment means; a plurality of light-emitting components having the first shape and at least two electrodes, received into at least some of the first recessed binding sites and electrically connected to the embedded interconnect network by the attachment means; and a plurality of light-detecting components having the second shape and at least two electrodes, received into at least some of the second recessed binding sites and electrically connected to the embedded interconnect network by the attachment means. The first shape and the second shape can be the same or different. If a similar shape is used for the first and second binding sites, then an additional feature of the two shapes will be different so as to enable selective deposition of each type of component. Examples of other characteristics that may vary include sizes of the shapes and material characteristics of the two different components (e.g., polarity of the surface of the component).

The number of different types of components (e.g., a plurality of light-emitting and light-detecting components) is not limited to two. Thus, the device may include multiple pluralities of light-emitting and/or light-detecting components in addition to other electronic and optical components.

The components are attached to the template by an attachment means. The attachment means can be any method, material, or surface treatment sufficient to direct the components to preferentially deposit in the recesses and then create a mechanical and electrical connection between the electrodes on the component and the electrodes in the recesses on the template. A preferred attachment means is a solder, as described in the exemplary embodiments below. A solder in molten form wets the metal electrodes in the recessed binding sites and the capillary force of the solder interacting with the metal electrodes on a component provides a force drawing the component into the recessed binding site. Cooling the solder completes the mechanical and electrical connection. The same solder can be used for all components, or a different solder (e.g., one with a different melting temperature) can be used for different components.

In an alternative embodiment, the attachment means is a solder that is in solid form (i.e., not heated above the melting temperature of the solder) when the components are assembled into the recesses. Once the components have been assembled into the recesses, the solder is then heated above its melting temperature and then cooled below the melting temperature, thus creating a mechanical and electrical connection between the electrodes on the component and the electrodes in the recesses on the template.

Additional attachment means include self-assembled monolayers (SAM) that have surface functionalities that facilitate the mechanical and electrical connection. An exemplary embodiment of a SAM attachment means is a SAM formed on the electrodes in the recessed binding site, where the SAM has thiol-terminated ends. If the component electrodes are made of gold, the well-known thiol-gold interaction will provide the mechanical connection between the electrodes and the SAM can facilitate electrical connection between the electrodes if the SAM is sufficiently thin or has sufficient electron conjugation to adequately conduct electricity between the electrodes. Other attachment means include using hydrophobic/hydrophilic surface treatments, electrostatic interactions, and antibody/antigen surface treatments.

The attachment means can be the same or different for each recessed binding site or each shape of recessed binding site.

The device can be operated by bringing the device into proximity with an analyte that is solid, liquid, or gaseous, such that at least some of the light-emitting components and at least some of the light-detecting components are in optical communication with the analyte. In one embodiment, the device includes a channel adapted to receive a fluid, where at least some of the light-emitting components and at least some of the light-detecting components are in optical communication with the channel.

Typical devices of the invention include light-emitting components and light-detecting components with electrodes formed on one side of the components. The electrodes on the components are typically formed so that there is one central electrode and one electrode situated between the central electrode and the edge of the component. The electrodes on the components are shaped and positioned so that electrical connection can be made with the electrodes in the recessed binding sites of the template. In one embodiment, the light-emitting component electrodes are formed on only one side of the light-emitting components and include a circular electrode substantially centered on the light-emitting component and an annular electrode disposed around the circular electrode.

In one embodiment, the first shape is one or more of: circular, square, rectangular, triangular, and cruciform.

Figure 1B:
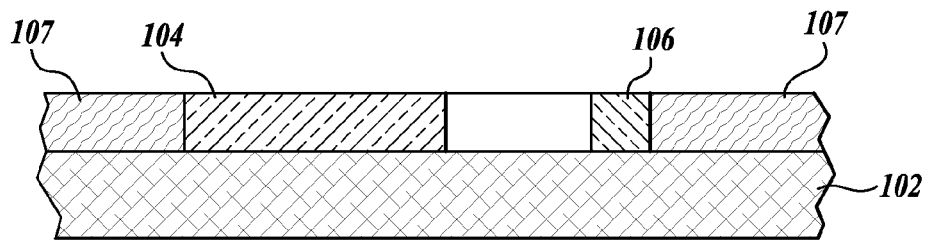
Figure 1C:
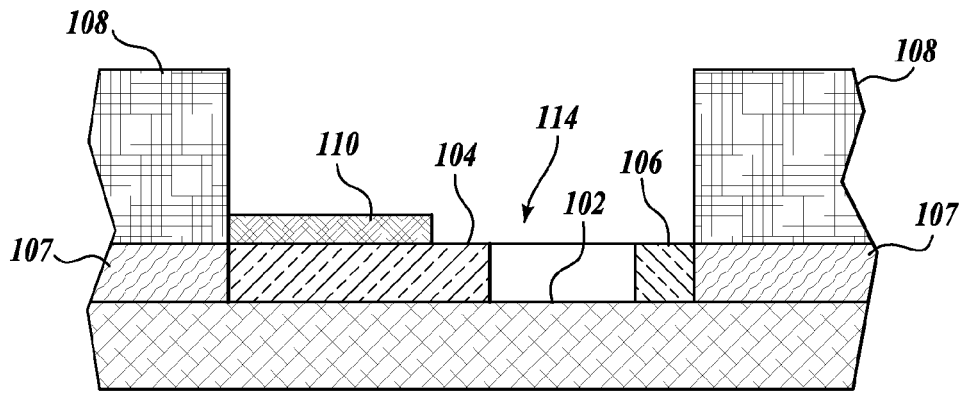
Figure 1D:
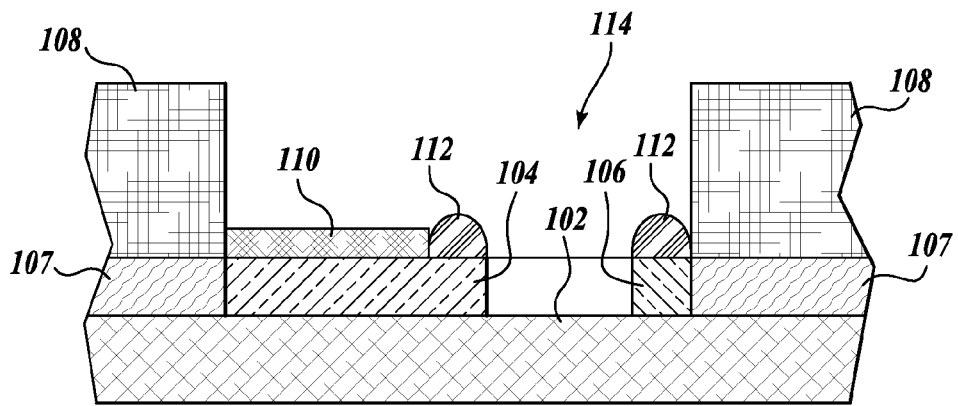
Figure 1E:
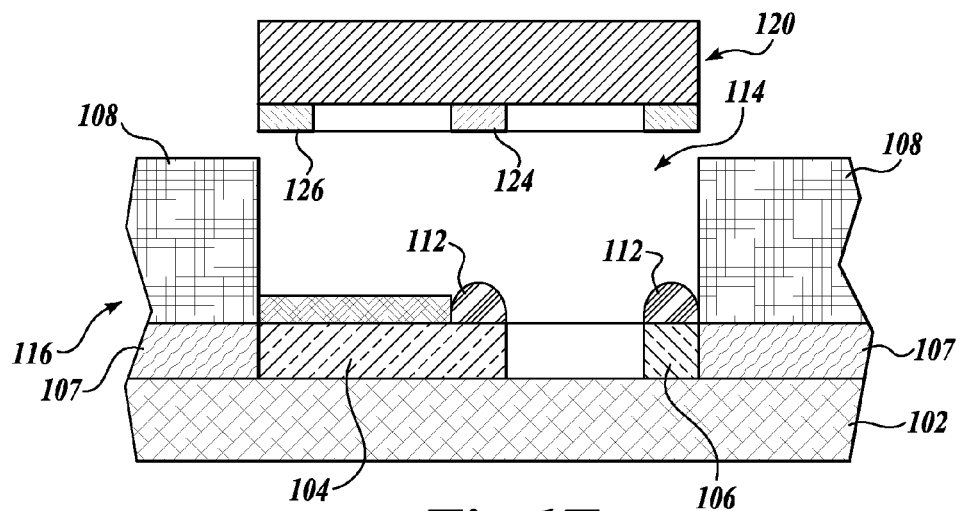
Figure 1F:
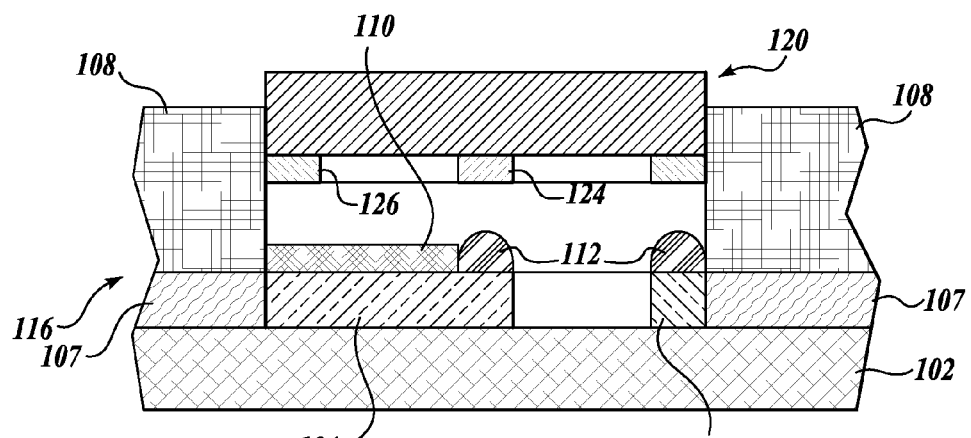
Figure 1G:
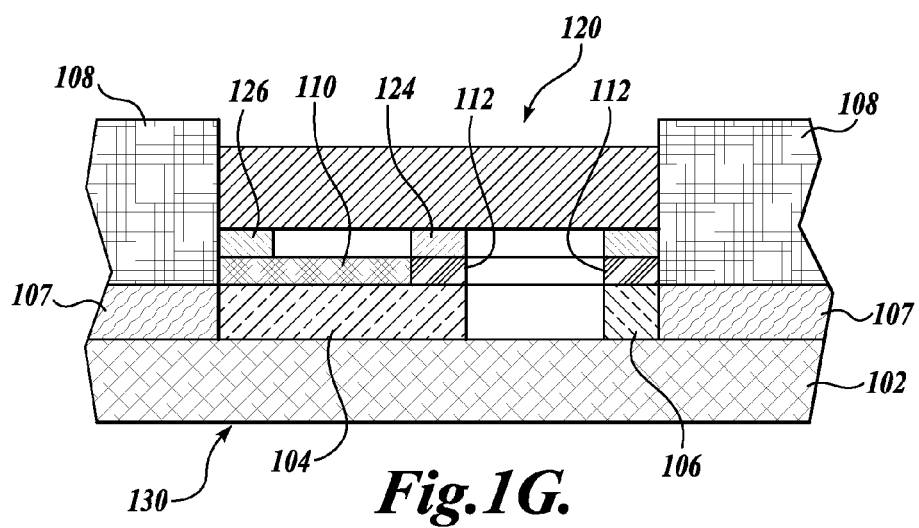

Referring now to FIGS. 1A-1G, which schematically show the fabrication of a representative device of the invention, wherein FIGS. 1A-1D illustrate fabrication of the template 116 and FIGS. 1E-1G illustrate self-assembly of components onto the template 116. FIG. 1A illustrates the beginning of fabrication with a substrate 102. The substrate 102 can be any material that will withstand typical microfabrication processes. Representative substrate materials include any of a number of materials including, but not limited to, polymer, glass, ceramic, semiconductor, and other inorganic or organic materials. In FIG. 1B, through conventional photolithography, an electrical network is patterned on the surface of the substrate, including an inner electrode 104, an outer electrode 106, and an interconnect network 107. The electrodes 104, 106 and the interconnect network 107 can all be deposited and/or patterned in the same lithographic step. In a preferred embodiment, the outer electrode 106 is in the shape of a circular arc. The electrodes 104, 106 are electrically connected to, or integrated with, the interconnect network 107. In FIG. 1C, a negative photoresist (e.g., the negative photoresist SU8) is used to pattern the binding site in two stages. First, a thin photoresist layer 110 is deposited so as to mask a portion of the inner electrode 104 and then a second, thicker, photoresist layer 108 is used to define the shape of the recessed binding site 114. After the two-stage deposition of the negative photoresist, the resulting structure will have a shape defined by the photoresist 108. The exposed metal surfaces include the outer electrode 106 and the inner electrode 104. The inner electrode 104 is substantially at the center of the binding site 114. The interconnect network 107 is embedded below the photoresist layer 108.

A means for attaching and electrically connecting components to the interconnect network 107 is then applied to the electrodes 104, 106. In this representative embodiment, the attachment means is a solder. Solder 112 is deposited onto the metallic surfaces through wetting, as illustrated in FIG. 1D. Preferably, the solder has a melting temperature of between about 40° C. and about 150° C. The template 116 is then placed in a fluid, heated to a temperature greater than the solder melting temperature, and optoelectronic components 120 are introduced, as illustrated in FIG. 1E. Agitation may be used to facilitate the deposition of the optoelectronic components 120 into the recessed binding sites 114.

The optoelectronic components 120 can be any type of optoelectronic device including, but not limited to, light emitting diodes (LEDs), photo detectors, vertical-cavity surface-emitting lasers (VCSEL), semiconductor lasers, and other optoelectronic devices known to those of skill in the art. Each component 120 includes a circular electrode 124 deposited near the center of the shape of the component 120, and an annular electrode 126, which typically forms a ring around the circular electrode 124 but does not contact it. The shape of the optoelectronic component 120 matches the shape of the recessed binding site 114 so as to facilitate the reception of the optoelectronic component into the recessed binding site.

Through agitation, capillary forces, and gravitational forces, as illustrated in FIG. 1F, the optoelectronic components 120 are received into the recessed binding sites 114 facilitated by the wetting effect and surface effects of the molten solder 112 interface with the optoelectronic component electrodes 124 and 126. The template is then cooled and the solder 112 solidifies, forming a mechanical and electrical contact between the electrodes 124, 126 of the optoelectronic component 120 and the electrodes 104, 106 of the recessed binding site 114. The completed assembly 130 is illustrated in FIG. 1G.

Figure 2:
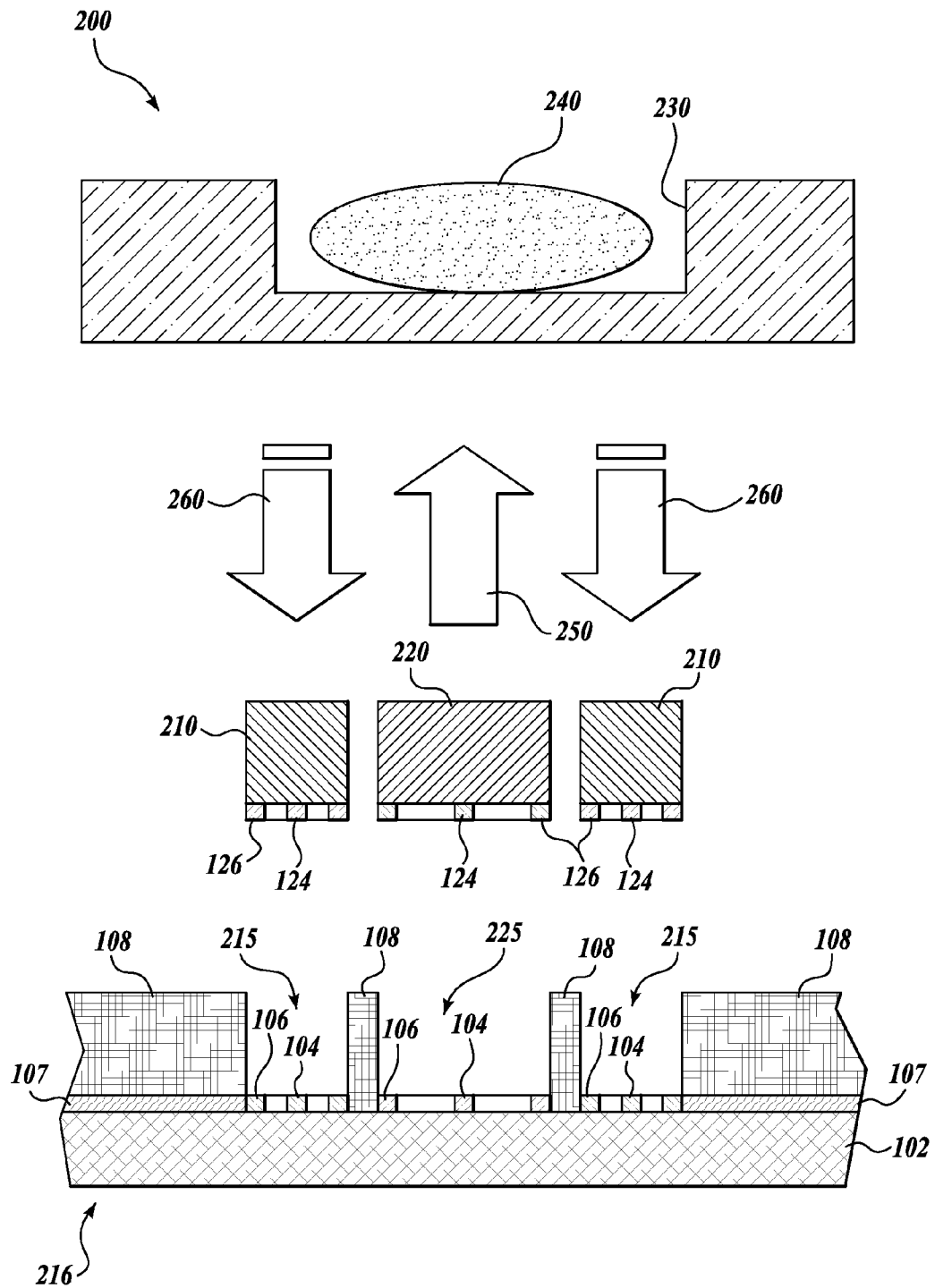
FIG. 2 is a cross-sectional sketch of the fabrication of a portion of a representative device in accordance with the present invention.

Referring now to FIG. 2, which shows an exploded schematic view of an optical analysis device 200 made in accordance with the teachings of the present invention. The optical analysis device 200 includes three main components or assemblies: (1) LECs 220; (2) LDCs 210, and (3) a template 216 comprising a substrate 102 patterned with electrodes 104, 106, attached to an interconnect network 107, and permanent photoresist 108 (e.g., the negative photoresist SU8) that serves as a shape-coded template to organize the freestanding components (LECs 220 and LDCs 210). In an exemplary embodiment, the LECs 220 fit into substantially circular recessed binding sites 225 defined by the photoresist 108 and the LDCs 210 fit into substantially square recessed binding sites 215 defined by the photoresist 108 on the substrate 102. The electrodes 104 and 106 patterned on the bottom surfaces of the recessed binding sites 215, 225 provide electrical connections to each of the LECs 220 and LDCs 210 (via component electrodes 124, 126) and the embedded interconnect network 107. In one embodiment, the LECs 220 are light-emitting diodes, semiconductor lasers, or vertical-cavity surface-emitting lasers. In one embodiment, the LDCs 210 are p-n junction photodetectors.

Also shown in FIG. 2 is an analyte 240 that can be, for example, in an array of microwells 230, microfluidic channels, or any structure adapted to receive a fluid. Excitation light 250 is emitted by the LEC 220 toward the target analyte 240, which has an optical response (e.g., fluorescence, reflection, or refraction). The emitted light 250 interacts with the analyte 240, and return light 260 is detected by one or more of the LDCs 210, thereby conveying information about the analyte 240.

Figure 3A:
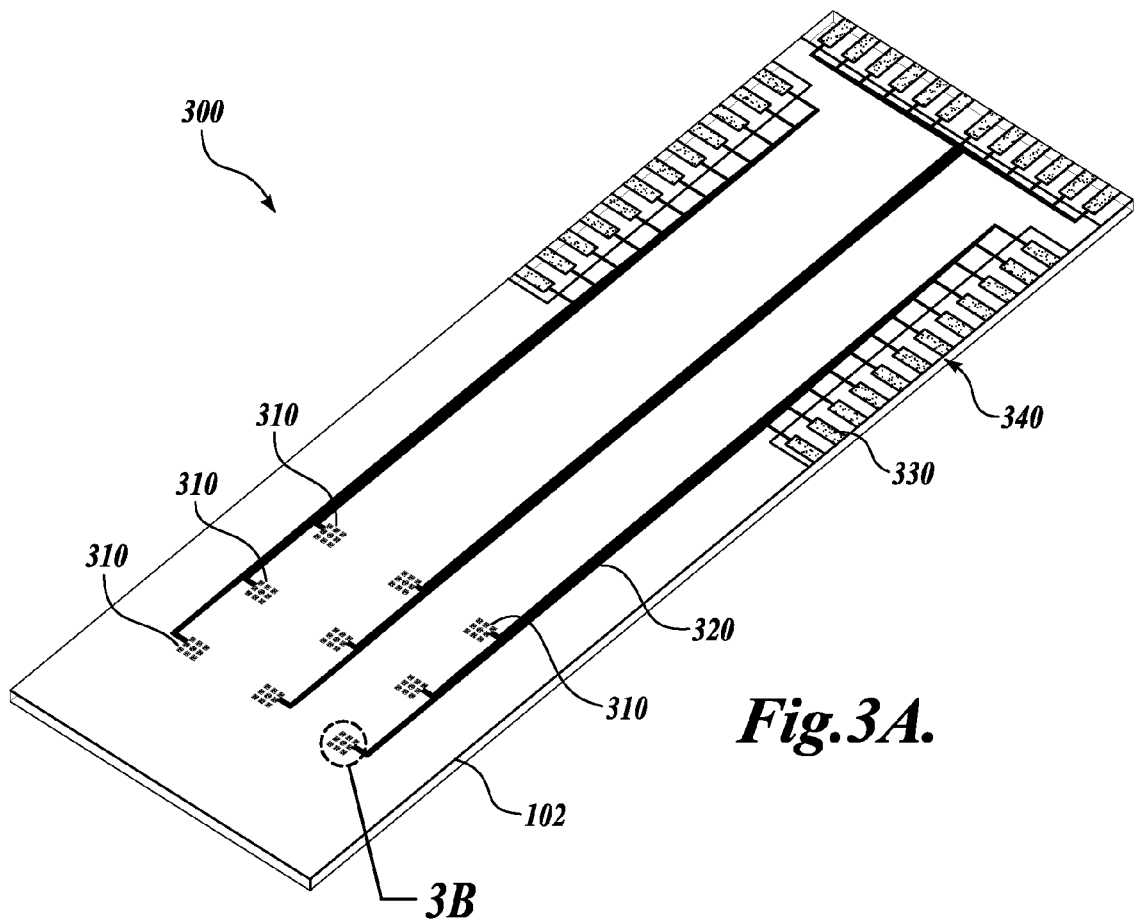
FIGS. 3A-3E illustrate the fabrication of a representative device in accordance with the present invention.

Referring now to FIG. 3A, an exemplary integrated optical analysis chip 300 comprises a 3×3 configuration of individually controllable emission/detection arrays 310 deposited on a substrate 102. Each array 310 is made up of a circular emission source LEC 220 (e.g., an LED) surrounded by eight square LDCs 210 (e.g., p-n junction photodiodes), as illustrated in more detail in FIG. 3B. The shape difference between the LEC 220 and the LDCs 210 (in this exemplary embodiment, square versus circular) allows the self-assembly process to utilize shape coding to guide the components 210, 220 to shape-specific locations. Each array 310 is connected by a substantially embedded interconnect network 107 (illustrated in detail in FIG. 3B) that includes electrical leads 320 running to electrical connections 330 that comprise part of an electrical input/output array 340 useful for integrating the emission/detection arrays 310 with external devices and/or networks.

The embedded interconnect network 107 provides the benefit of parallel components interfaced with a broad network while preserving the selective and targeted self-assembly afforded by having the metal in the binding sites as the only metal exposed near the arrays 310. In the exemplary embodiment described above where the attachment means is solder, the solder will wet only the metal portions of the recessed binding site (specifically the inner electrode 104 and outer electrode 106) and the electrodes 124, 126 of the optoelectronic component 120. Because the interconnect network 107 is embedded, it is not wetted by the solder. In one embodiment, the embedded interconnect network 107 is deposited before the deposition of the material used to form the recessed binding sites.

Figure 3B:
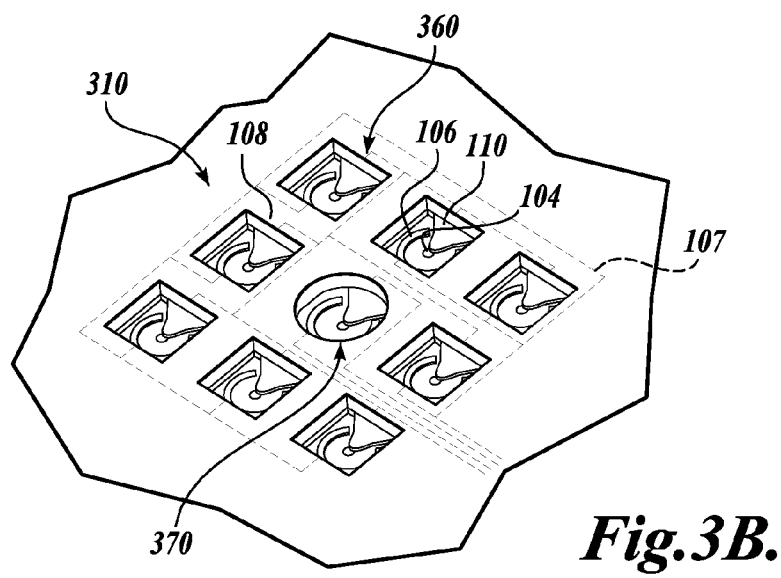

FIG. 3B is a detailed view of an emission/detection array 310 having first shape recessed binding sites 360 (square), and second shape recessed binding sites 370 (circular), prior to self-assembly. The shapes are defined by thick photoresist 108. Each binding site has an inner electrode 104, an outer electrode 106, and thin photoresist 110 covering all but the central tip of the inner electrode 104.

Figure 3C:
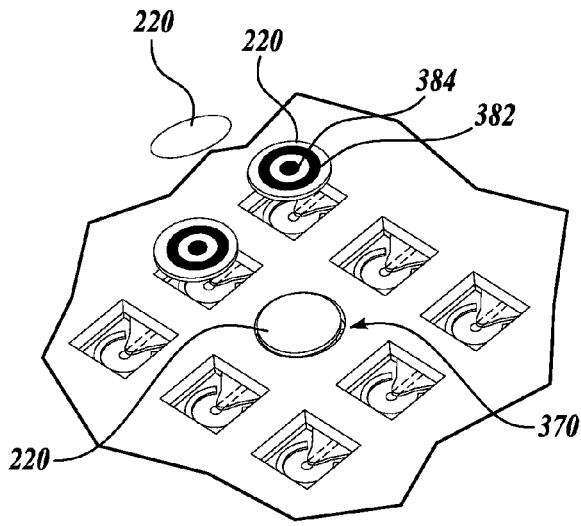
Figure 3D:
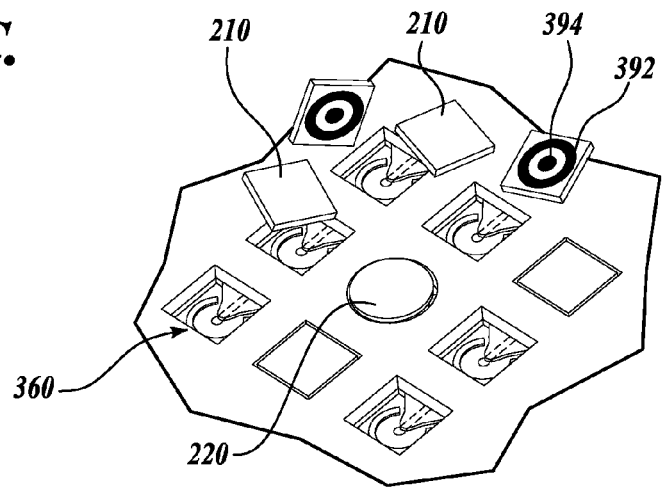
Figure 3E:
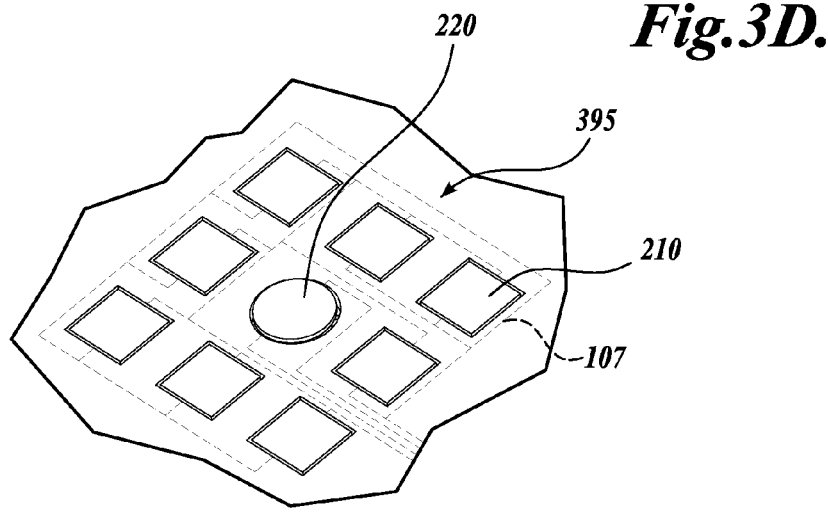
Figure 4:
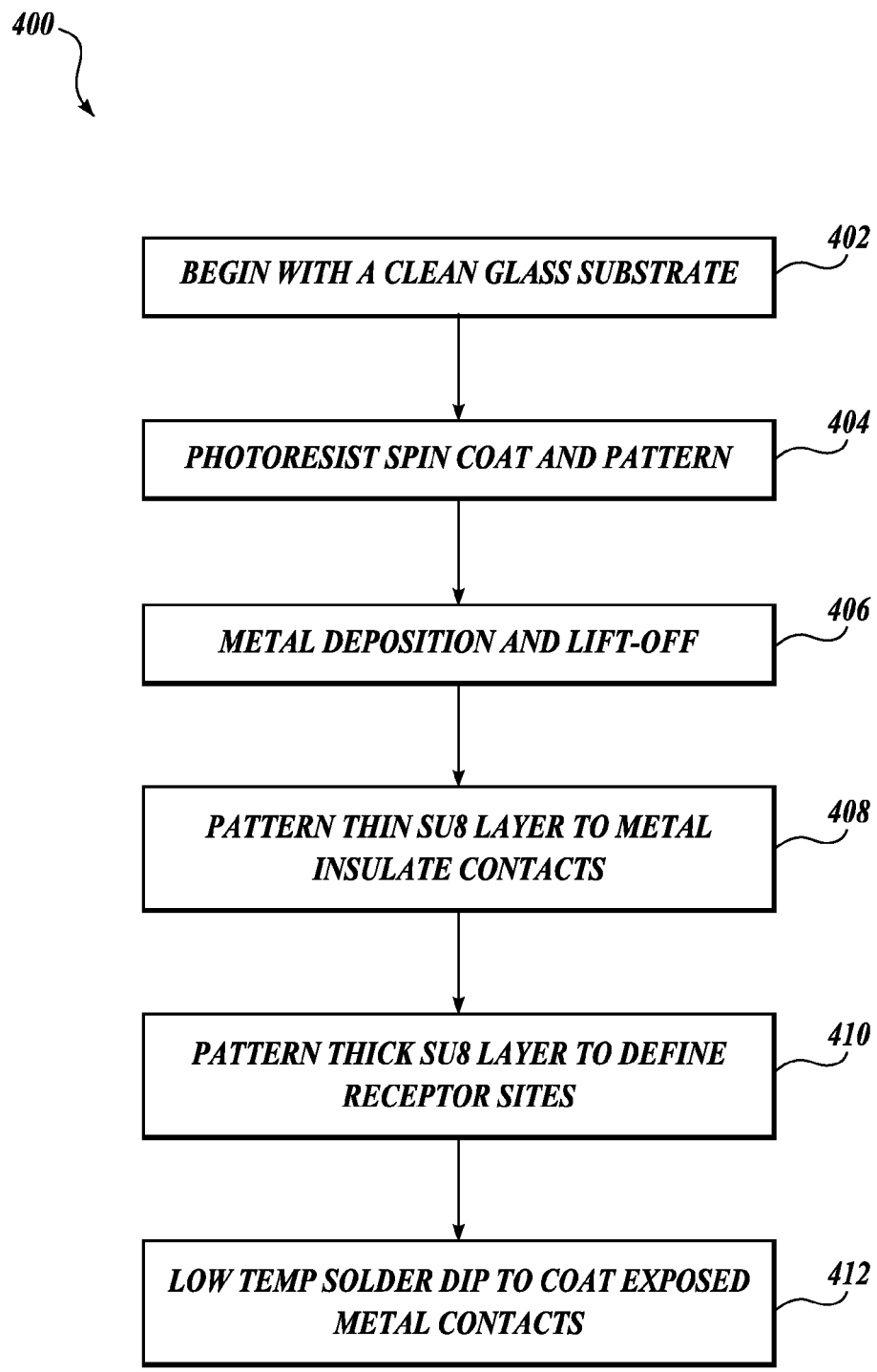
FIG. 4 is a flow chart of a representative process for fabricating a template in accordance with the present invention.

The shape and dimensions of each of the LECs 220 and LDCs 210 are carefully selected so that the circular LECs 220 will not fit into the recesses defined by the binding site 360. The LECs 220 have a diameter larger than the width of the square LDCs 210, in this exemplary embodiment. The components 210, 220 can be deposited one type (e.g., LEC) at a time or simultaneously. In an exemplary embodiment, the LECs 220 are first fluidically self-assembled, as shown in FIG. 3C, such that the circular recessed binding sites 370 are occupied by an LEC 220 prior to introducing the square LDCs 210. The LECs 220 and LDCs 210 both have a center electrode 384, 394 and an annular electrode 382, 392. Once the LECs 220 have been received into circular recessed binding sites 370, the square LDCs 210 are fluidically self-assembled as shown in FIG. 3D, which results in the final assembled configuration containing an emission/detection unit 395 as shown in FIG. 3E. The assembled unit 395 includes electrodes 104 and 106, illustrated in FIG. 3A, (not shown in FIG. 3E) that connect the unit 395 and the optoelectronic components 210, 220 to an embedded interconnect network 107, allowing for the unit 395 to be connected to other units and other devices, including a computer or computer network. The emission/detection unit 395 is typically an array of structures similar to those illustrated in FIG. 1G, specifically the connected assembly 130. The components are electrically connected to the embedded interconnect network 107 using an attachment means (e.g., solder).

An exemplary fabrication process 400 for preparing a substrate for use in the method of the invention is outlined in FIG.

4. The fabrication process 400 begins with a substrate, such as a clean borosilicate glass wafer, that may be prepared using standard glass wafer cleaning protocols 402. After priming the wafer, a positive photoresist, such as AZ4620, is spun onto the wafer, and the wafer is exposed and developed to pattern the mask for electrical interconnects 404. The electrodes are then patterned 406. Typical electrode deposition methods include sputtering and e-beam evaporation. In this exemplary embodiment, the metal layers deposited for the interconnects are 10 nm Ti/W, 90 nm Ni, followed by 80 nm of Au. The Ni layer serves to create a barrier layer for the low temperature solder that is used during the representative self-assembly process described previously, while the Au layer is used because it is easily wetted by the solder. After sputtering the metal contacts, the wafer is placed in acetone for lift-off.

After patterning the electrodes, an insulating layer is deposited and patterned 408. In a representative example, a first layer of photoresist is a thin 1.2 micron layer that insulates portions of the electrodes to prevent shorting after self-assembly. A second, typically thicker, layer of photoresist is then patterned 410. The second layer serves to define the shapes for each of the recessed binding sites (e.g., as a circle or square). The second layer is thicker to ensure proper seating of the LECs 220 and LDCs 210 as they assemble into the recessed binding sites. For components ranging from 5 to 10 microns in thickness, a photoresist layer of 15 to 20 microns is typical.

In this exemplary embodiment, when all of the layers have been patterned, the wafer is diced into 1"×3" chips and the chips are solder dipped 412 using a low-melting-point solder alloy (Indium Corporation). The solder dipping is done in a heated glass beaker that contains the solder alloy and a solution of ethylene glycol and HCl, with a combined pH of between about 1 and about 2. The solution acidity serves to remove the oxide layer on the solder alloy and allows for the solder to be successfully wetted on the exposed gold contacts on the template chips.

Upon wetting with solder, only the exposed metal portions of the template are wetted, while areas insulated and covered by the photoresist are not. After the template is prepared with an attachment means, the components are assembled.

Figure 5:
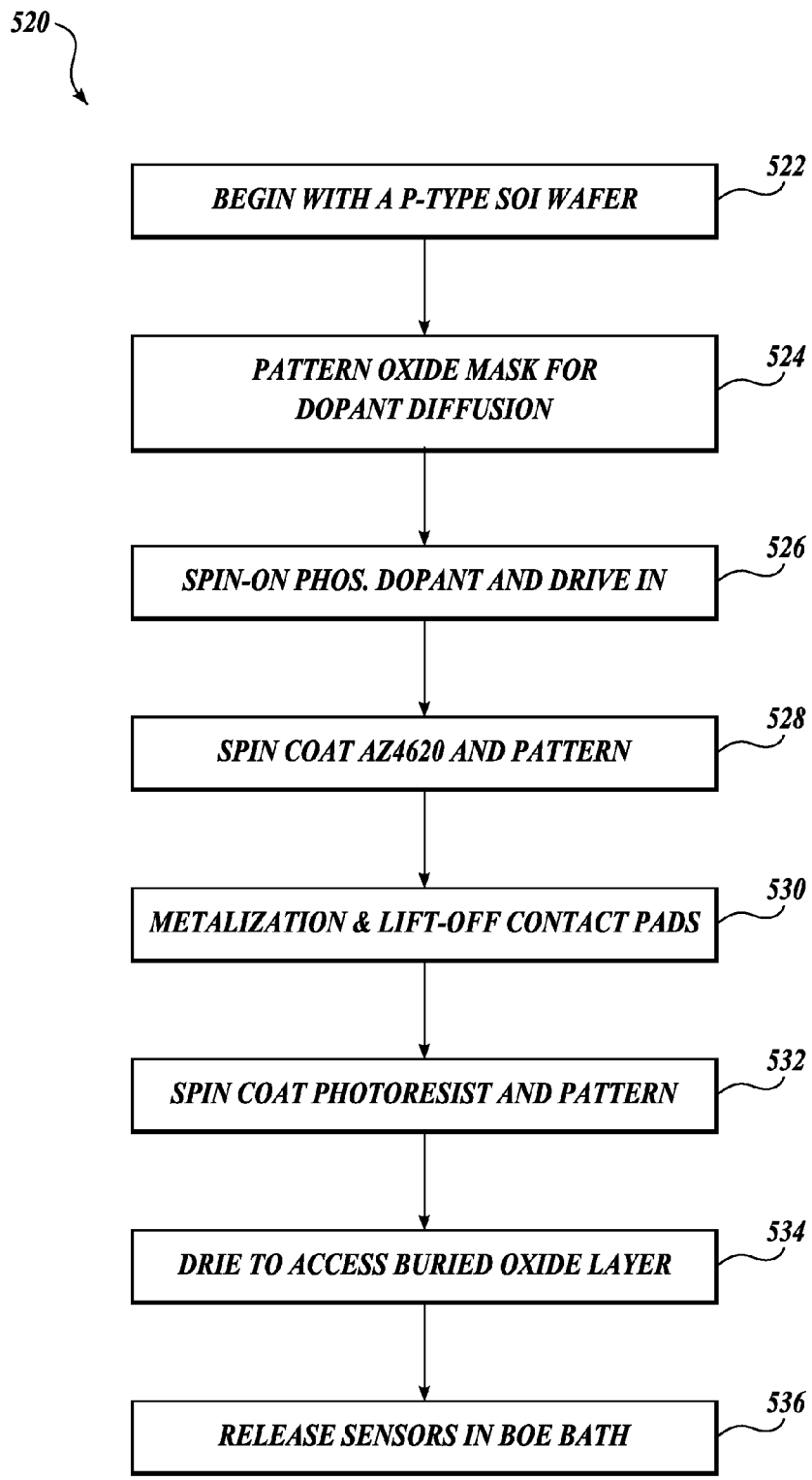
FIG. 5 is a flow chart of a representative process flow for fabricating a silicon photodiode useful in the present invention.

There are many options for LDCs 210, and in a representative embodiment a silicon p-n junction photodiode structure is used. An exemplary process flow 520 for LDC 210 fabrication is depicted in FIG. 5. The beginning substrate is a p-type silicon on glass (SOI) wafer that may be cleaned using standard wafer cleaning protocols 522. The wafer is then placed into an oxidation furnace to grow a 500 nm wet oxide layer 524. The wafer is primed, patterned with photoresist (for example AZ4620), exposed, and developed to expose portions of the oxide layer using standard photolithography processes. The wafer is placed into a buffered oxide etch (BOE) to etch away the exposed portions of the oxide layer and to expose the bare silicon underneath. The resulting oxide mask, in an exemplary embodiment, is an array of rings. The photoresist is then stripped, leaving only the patterned oxide mask on silicon. A phosphorous spin-on dopant (such as Honeywell P-8545) is used to spin on a thin layer of dopant onto the wafer surface 526. The wafer is placed into a diffusion furnace to drive in the phosphorous, thus creating a p-n junction. The wafer is placed in BOE again to remove both the oxide mask and the remaining spin-on dopant.

Once the diffusion has taken place and the oxide mask has been stripped, metal contacts are evaporated onto the wafer. To define the shapes of the metal contacts, a photoresist mask is patterned 528. Metal contacts are then patterned 530. In an exemplary embodiment, the wafers are placed into an e-beam evaporator to deposit 20 nm Cr and 200 nm Au for metal contacts. The Cr layer provides adhesion to the silicon substrate and the Au is used for its wetting qualities (e.g., with solder). Once the contacts have been deposited, the wafers are placed in acetone for lift-off of the exposed photoresist areas. The components are patterned one last time with photoresist to define the final square shapes of the LDCs 532.

After the components have been patterned with photoresist, they are etched with a deep reactive ion etching (DRIE) system 534, wherein a standard Bosch protocol is applied to etch through the silicon device layer down to the buried oxide layer. The entire wafer is placed in 49% HF to etch away the buried oxide layer 536. This releases the LDC components yielding a powder-like collection of components. The released LDC components are then diluted in water and gathered using a filter.

The functionality of the released photodiode LDC components 210 can be verified using a probe station and a ~0.7 mW/mm$^2$ HeNe laser with an emission wavelength of 632 nm. Under −0.5 V reverse bias a 60,000-fold increase in reverse saturation current can be observed for representative devices.

Figure 6:
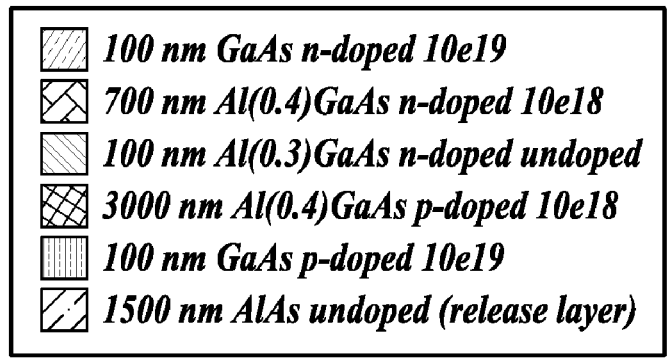
FIG. 6 is a graphical representation indicating the layers of a light-emitting diode structure useful in the present invention.
Figure 6:
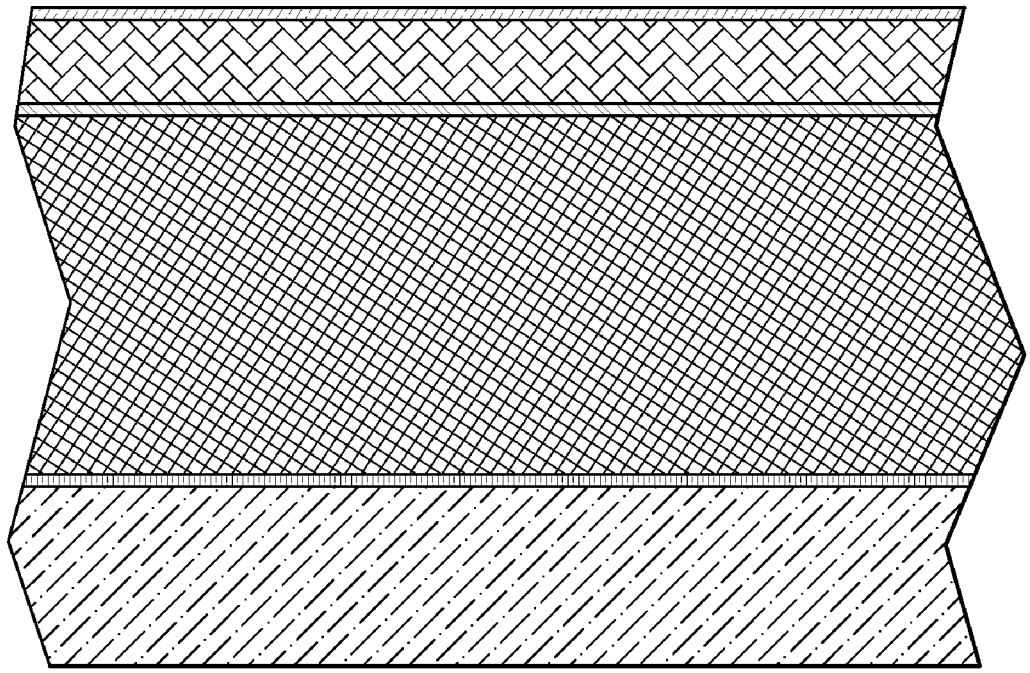

Representative LECs useful in the invention are light-emitting diodes (LED). A typical device is an AlGaAs LED double-heterojunction structure grown on an AlAs sacrificial layer using a chemical vapor deposition (CVD) process. The layer thicknesses, alloy composition, and doping levels of the LED structure are indicated in FIG. 6. The active region in each LED is a 100 nm $Al_{0.3}Ga_{0.7}As$ intermediate larger bandgap $Al_{0.4}Ga_{0.6}As$ layers. The Al concentration has a relationship to the bandgap:

$$E_g = 1.424 + 1.247\, x \text{ eV} \tag{1}$$

where x is the concentration of Al. The active region has a bandgap of 1.8 eV, which translates to a peak emission wavelength of 689 nm.

Figure 7:
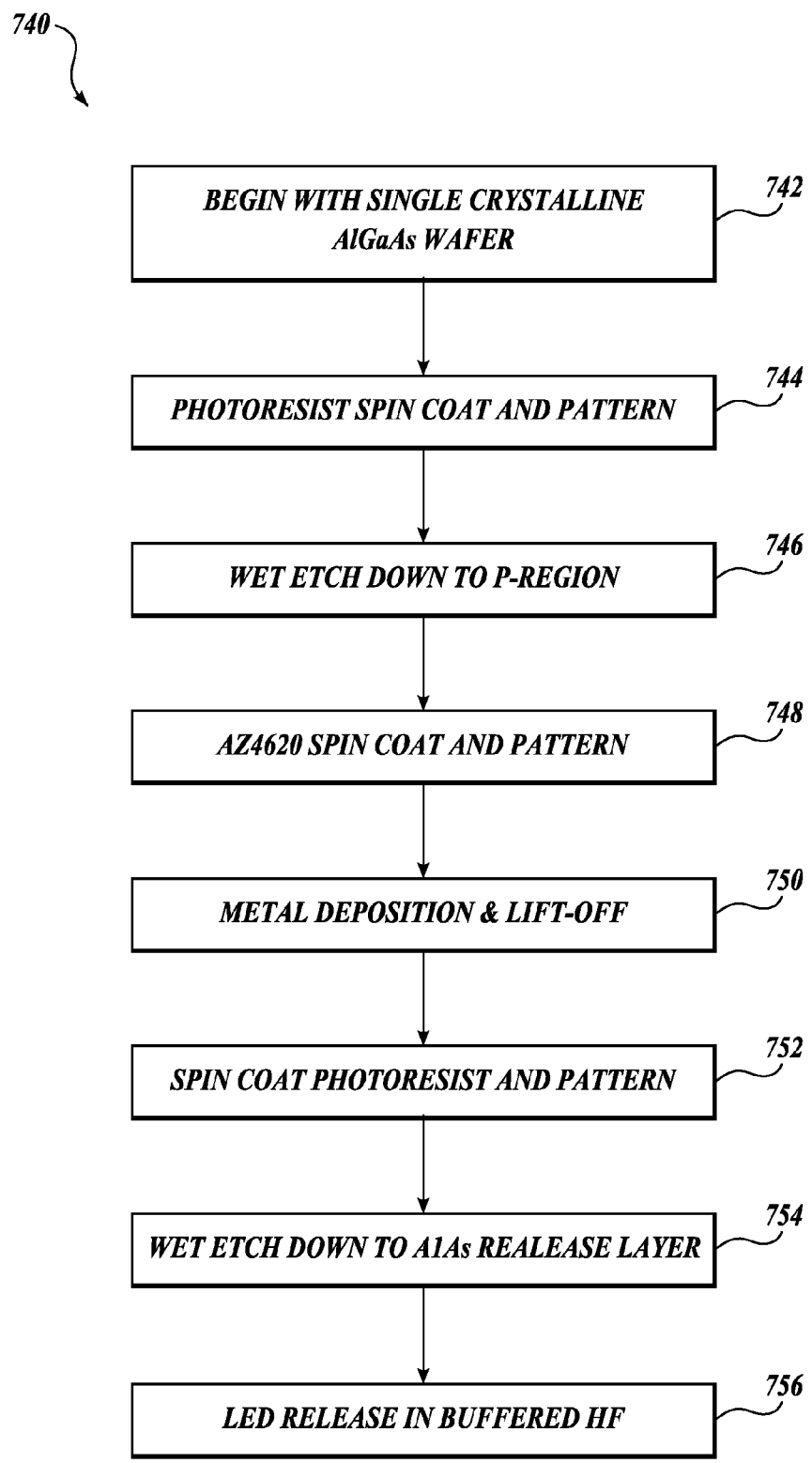
FIG. 7 is a flow chart of a representative process flow for fabricating of a light-emitting diode useful in the present invention.

An exemplary fabrication process 740 for LEDs is outlined in FIG. 7. Starting with a clean substrate 742 (in this example, a multilayer AlGaAs wafer), patterning is done with photoresist exposed and developed using standard photolithography processes 744. A wet etch in 15:1 citric acid:hydrogen peroxide is used to etch down 1.2 μm through the top three layers to the first p-region from the top. This etch gives access to the p-region surface so that metal contacts can be patterned onto the p-side of the LED structure. After etching to the p-region, the photoresist is stripped and new layer of photoresist is patterned onto the wafer 746. This photoresist mask is used for patterning the metal contacts onto the top n-region and onto the exposed p-region in the center of the LED. An exemplary metallization process includes placing the wafer in an MRC Sputtersphere for the deposition of 50 nm Ti/W, 90 nm Ni, 100 nm Au, followed by lift-off 748 to define the electrodes of the LEDs. Next, the wafers are patterned again 750 with photoresist, which defines the circular shapes of the LEDs after masking and exposure. The photoresist-patterned wafer is etched 752 in 15:1 citric acid:hydrogen peroxide down to the AlAs release layer. AlAs etches very quickly in HF, and therefore acts as a sacrificial layer. The LEDs are released 754 by etching through the release layer with a 49% HF etch yielding a powder-like collection of components. The released LEDs are typically diluted with water, filtered, and collected for use in self-assembly.

The forces at work in a representative self-assembly process include: (1) gravitational forces, (2) capillary forces of the attachment means (e.g., solder wetting the contacts on the components), (3) fluidic flow pushing the components across the surface of the template, (4) shape-coded matching of components to recessed binding sites, and (5) external agitation. Additional forces useful for self-assembly include magnetic (e.g., using magnetic field gradients to assemble components), surface tension (e.g., using an air-fluid interface to direct components), and electrostatic (e.g., using an electric field gradients to assemble components). These forces combine to guide the components to shape-coded recesses on the template. In the self-assembly process, a typical first step is the fabrication of the freestanding components and the template (e.g., using the methods described above). The fabrication processes described above yield two vials of components, each containing a fluidic slurry: one vial containing circular LECs 220 and the other vial containing square LDCs 210.

Prior to assembly, the optoelectronic components 210 and 220 are cleaned to ensure that proper wetting occurs between the solder and the electrodes on the components. For example, to clean the LDCs 210, a piranha etch solution (3:1 sulfuric acid:hydrogen peroxide) for 3 minutes directly in the vial containing the released LDCs 210 is typical. The piranha etch removes any organic material that may have built up on the surface of the contacts and cleans the electrodes.

The LECs 220 may be cleaned, for example, using 0.1N HCl for 3 minutes, because AlGaAs is rapidly etched in piranha. Once the optoelectronic components 210, 220 have been cleaned, they are put into ethylene glycol and introduced into the self-assembly environment.

Self-assembly is typically conducted in a heated fluidic environment. In a current embodiment, ethylene glycol is used as the carrier fluid for its mechanical and chemical characteristics. A carrier fluid is typically selected based on a number of factors: a boiling temperature greater above the melting temperature of the solder; ability to create an acidic environment; lack of corrosive effects on the solder, and a viscosity that allows for free movement of the components. Typically, HCl is added to the ethylene glycol to attain a pH level between 1.0 and 2.0. The acidity dissolves the oxides that continually form on the surface of the solder that has been wetted onto the contacts of the device-containing chip 300. The solder-dipped template is placed in a glass beaker and immersed in the acidic ethylene glycol solution. The entire self assembly environment is brought to 65° C. using a temperature-controlled hotplate. When the solution temperature is greater than the melting temperature of the solder, the solder on the template chip is in a molten state and ready for assembly.

Agitation is initiated and the cleaned optoelectronic components 210, 220 are sequentially introduced into the heated acidic ethylene glycol environment. Any means of actuation are suitable for agitation. Representative types of agitation include optical, mechanical, acoustic, electrical, and magnetic. Typical agitation methods include: sonication, mechanical motors with offset weights, solenoids, pneumatic actuators, piezo actuators, using speakers or acoustic vibrations, ultrasonic vibrations, optically induced agitation (e.g., laser tweezer), oscillating magnetic fields, and oscillating electronic fields (RF). As the LECs 220 (and later, the LDCs 210) flow over the circular recesses 370 and square recesses 360, if the shapes match, the optoelectronic components 210, 220 will fit into the recesses. If the component is correctly oriented into the recessed binding site, the attachment means (e.g., solder) brings the component into proper alignment and creates a mechanical and electrical connection, typically through capillary forces. If the component is upside-down, then the fluid flow is able to remove the incorrectly assembled component because there is no adhesion force. Upon cooling the solution to a temperature below the melting temperature of the solder, the solder solidifies and the electrical/mechanical connection is strengthened.

Figure 8:
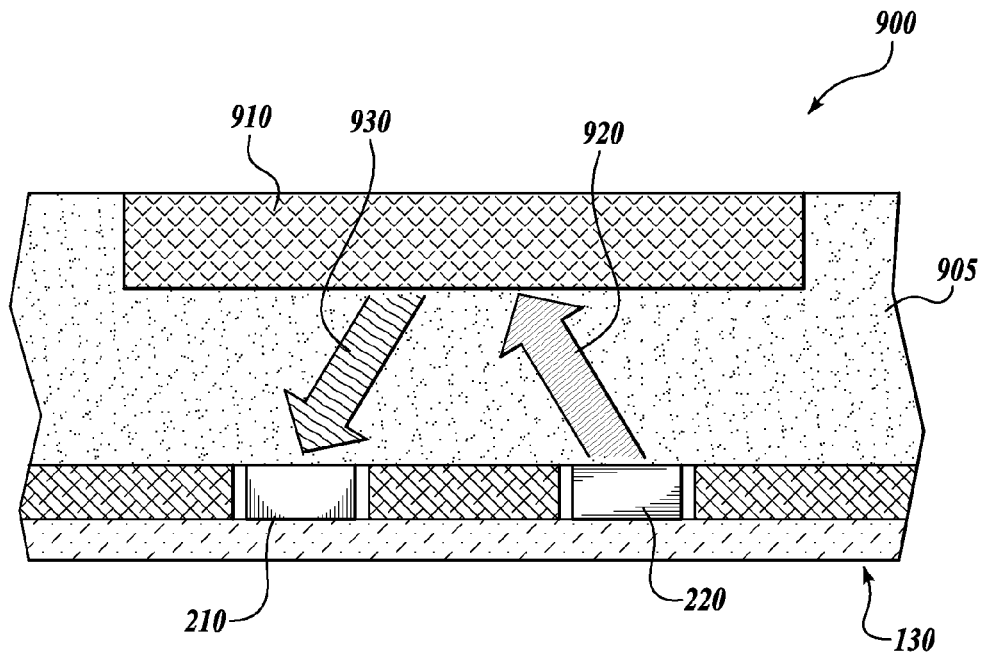
FIG. 8 illustrates a representative device in accordance with the present invention.

Devices of the invention can take several configurations, each having particular benefits. FIG. 8 illustrates a device structure 900 that includes a connected assembly 130 having an LEC 220 emitting light 920 and an LDC 210 adapted to receive light 930 that has interacted with an analyte 910 that is in optical communication with the optoelectronic components. The analyte 910 may be provided in a channel that is typically static (e.g., a well plate) or active (e.g., a microfluidic channel). The analyte 910 is typically separated from the components 220, 210 by a medium 905 that is typically transparent at wavelengths relevant to the analysis being performed. The medium 905 is typically a polymer or glass.

In one embodiment, the plurality of light-emitting components include a first plurality of light-emitting components having a first emission spectrum and a second plurality of light-emitting components having a second emission spectrum, where the first emission spectrum and the second emission spectrum are different.

In one embodiment, the plurality of light-detecting components include a first plurality of light-sensing components having a first absorption spectrum and a second plurality of light-sensing components having a second absorption spectrum, where the first absorption spectrum and the second absorption spectrum are different. Light-detecting components can be made of different materials and, as a result, have different absorption spectra. Alternatively, differently light-sensing abilities can result by integrating optical filters onto similar light-detecting components. If different filters are used on similar components, the wavelength of light that the component is sensitive to will be affected by the filters.

Figure 9:
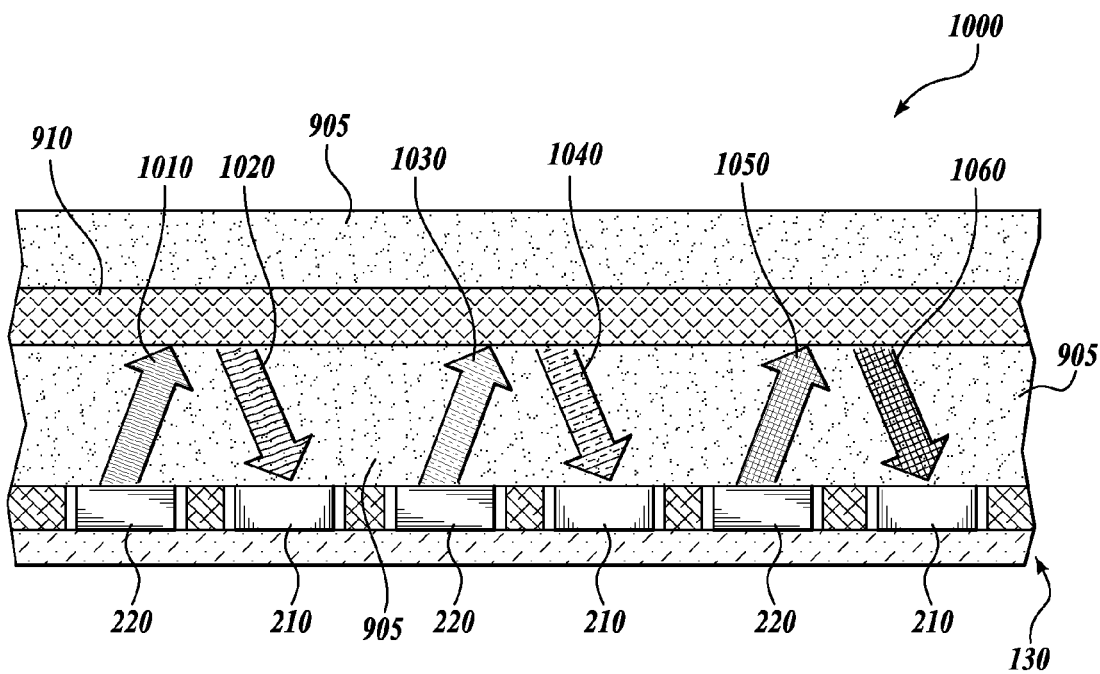
FIG. 9 illustrates a representative device in accordance with the present invention.

A multiplexed version of the device illustrated in FIG. 8 is illustrated in FIG. 9. The device 1000 includes several LECs 220 and LDC 210 that operate at different wavelengths. In a representative embodiment, the components 220, 210 are paired so that an LEC 220 and LDC 210 that are in close proximity will have an emission 1010 that will elicit a response from the analyte 910 at a wavelength 1020 that will be detectable by the LDC 210. Multiple pairings 1030, 1040 and 1050, 1060 yield the ability to probe and detect several wavelengths of light, and thus, possibly several analytes, or several spectral regions of an analyte. Alternatively, if all LECs 220 and LDCs 210 are the same, a parallel analytical system can be realized that will provide greater measurement accuracy through statistical averaging across the device.

Figure 10:
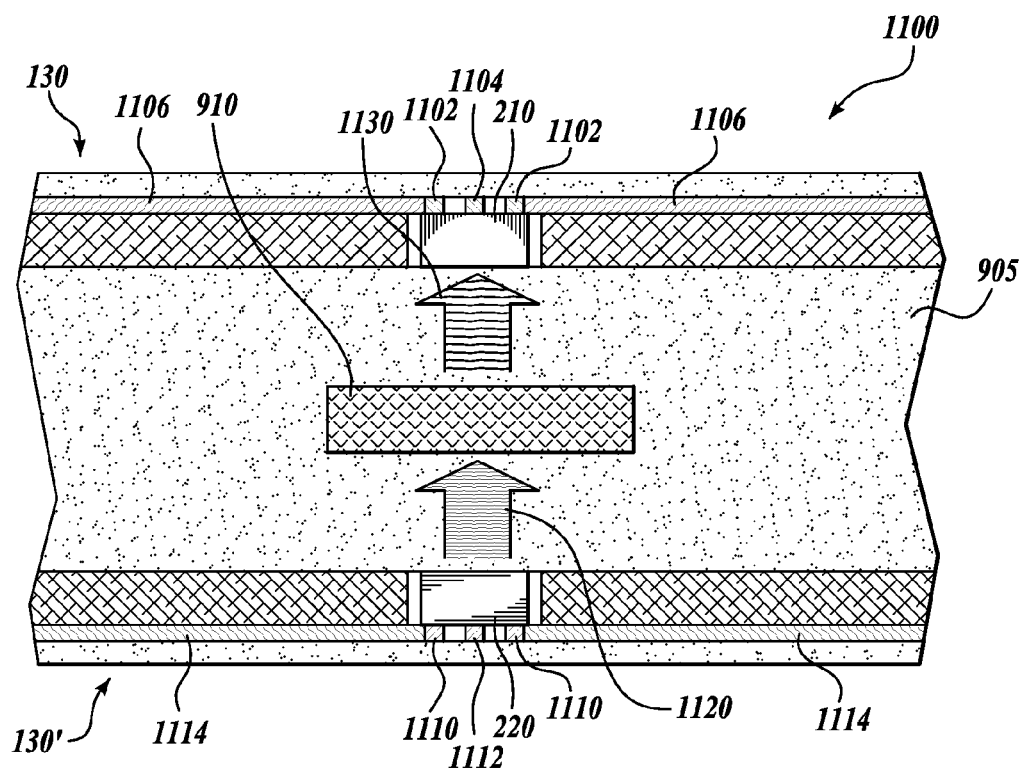
FIG. 10 illustrates a representative device in accordance with the present invention.
Figure 11:
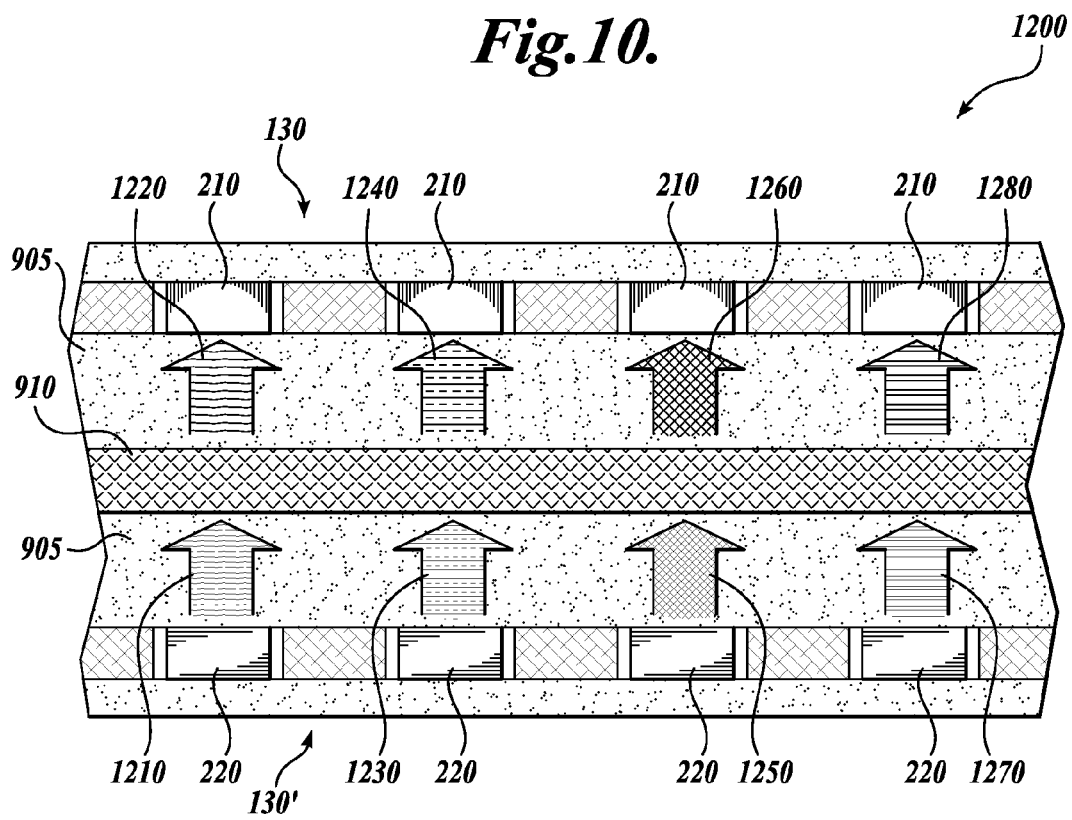
FIG. 11 illustrates a representative device in accordance with the present invention.

The devices illustrated in FIGS. 8 and 9 rely on luminescence or reflectance/scattering to detect the analyte. By assembling two different templates using the methods of the invention and then interfacing the two templates around an analyte 910, transmission analysis can be performed in addition to luminescence analysis. FIG. 10 illustrates a device that has two received and connected component templates 130, 130' one having an LEC 220 and another having a LDC 210. A medium 905 having an analyte 910 intermediate the components 220, 210 completes the device. Emission 1120 from the LEC 220 interacts with the analyte 910 and the altered light 1130 is detected by the LDC 210. Component template 130' includes a first embedded interconnect network 1114, similar to that of FIG. 2, which provides electrical connection to electrodes 1110 and 1112, which are in turn electrically connected to the LEC 220. Similarly, component template 130 includes a second embedded interconnect network 1106, providing electrical connection to electrodes 1102 and 1104, which are in turn electrically connected to the LDC 210. A multiplexed version is illustrated in FIG. 11, the device 1200 having several LECs 220 emitting light 1210, 1230, 1250, 1270 that interacts with the analyte 910 and the output light 1220, 1240, 1260, 1280 is detected by the LDCs 210.

While the medium 905 is passive in the above examples, meaning it does not significantly affect the emitted light (e.g., 1120) or detected light (e.g., 1130), by using a medium 905 that has light altering (e.g., filtering, enhancing, or shifting) properties, devices of the invention may be improved for particular analytes 905, LECs 220, and/or LDCs 210.

In one embodiment, the light-emitting components and the light-detecting components are components in a fluorescence analysis system. Optical analytical techniques are known to those of skill in the art. Representative optical analytical techniques include fluorescence, phosphorescence, reflection, refraction, scattering, and transmission techniques.

As described above, the optical devices of the invention can be assembled in a number of configurations, including LECs and LDCs on a single substrate or multiple substrates. Thus, in another aspect, the device includes a first template having a plurality of first recessed binding sites with a first shape, the first template having a first embedded interconnect network interconnecting the first recessed binding sites, where each of the first recessed binding sites contains an attachment means; a plurality of light-emitting components having the first shape and at least two electrodes, received into at least some of the first recessed binding sites and electrically connected to the first embedded interconnect network by the attachment means; a second template having a plurality of second recessed binding sites with a second shape, the second template having a second embedded interconnect network interconnecting the second recessed binding sites, where each of the second recessed binding sites contains an attachment means; and a plurality of light-detecting components having the second shape and at least two electrodes, received into at least some of the second recessed binding sites and electrically connected to the second embedded interconnect network by the attachment means. In one embodiment, the device also includes a channel adapted to receive a fluid, positioned such that at least some of the light-emitting components and at least some of the light-detecting components are in optical communication with the channel.

In the above-described devices, the components may all be deposited on the same substrate. Thus, in one embodiment, the first template and the second template are part of a unitary template.

Whether the components are deposited on the same template or two independent templates, the embedded interconnect networks on the singular or multiple templates may be connected and interfaced. In one embodiment, the first embedded interconnect network and the second embedded interconnect network are connected.

In another aspect, methods for making optical analysis devices of the invention are also provided, as described above. In this embodiment, the invention provides a method for fabricating an optical analysis device on a single template. In one embodiment, the method includes fabricating a plurality of freestanding light-emitting components having a first shape and at least two electrodes; fabricating a plurality of freestanding light-detecting components having a second shape and at least two electrodes; fabricating a template having: i) an embedded interconnect network; ii) a plurality of first recessed binding sites shaped to receive the light-emitting components; and iii) a plurality of second recessed binding sites shaped to receive the light-detecting components; providing an attachment means in the first and second recessed binding sites; immersing the template in a liquid; introducing the plurality of freestanding light-emitting components and the plurality of freestanding light-detecting components into the liquid such that at least some of the light-emitting components are received into at least some of the first recessed binding sites and at least some of the light-detecting components are received into at least some of the second recessed binding sites such that the received light-emitting components and the received light-detecting components are electrically connected to the embedded interconnect network by the attachment means.

In one embodiment, the method includes providing a channel adapted to receive a fluid and positioning the channel such that it is in optical communication with at least some of the light-emitting components and at least some of the light-detecting components.

In one embodiment, the attachment means is a solder. In this embodiment, the method further includes heating the liquid to a temperature sufficient to melt the solder and then cooling the template such that the solder solidifies after the components have been received into the recessed binding sites, thereby electrically connecting the received light-emitting components and the received light-detecting components to the embedded interconnect network.

In one embodiment, the first liquid and the second liquid are the same.

In another aspect, the invention provides a method for fabricating an optical analysis device having two templates. In this embodiment, the method includes fabricating a plurality of freestanding light-emitting components having a first shape and at least two electrodes; fabricating a first template having a first embedded interconnect network and a plurality of first recessed binding sites shaped to receive the light-emitting components, where the first recessed binding sites contains an attachment means that is electrically connected to the first embedded interconnect network; immersing the first template in a first liquid; introducing the plurality of freestanding light-emitting components into the first liquid such that at least some of the light-emitting components are received into at least some of the first recessed binding sites such that the received light-emitting component are electrically connected to the embedded interconnect network by the attachment means; fabricating a plurality of freestanding light-detecting components having a second shape and at least two electrodes; fabricating a second template having a plurality of second recessed binding sites shaped to receive the light-detecting components, where the second recessed binding sites contains an attachment means that is electrically connected to a second embedded interconnect network; immersing the second template in a second liquid; introducing the plurality of freestanding light-detecting components into the second liquid such that at least some of the light-detecting components are received into at least some of the second recessed binding sites such that the received light-detecting components are electrically connected to the embedded interconnect network by the attachment means.

In one embodiment, the method includes providing a channel adapted to receive a fluid and positioning the channel such that it is in optical communication with at least some of the light-emitting components and at least some of the light-detecting components.

In one embodiment, the attachment means is a solder. In this embodiment, the method further includes heating the first liquid to a temperature sufficient to melt the solder and heating the second liquid to a temperature sufficient to melt the solder. This embodiment also includes cooling the first template and the second template such that the solder solidifies after the light-emitting components and the light-detecting components have been received into the recessed binding sites on the first template and the second template, thereby electrically connecting the received light-emitting components to the first embedded interconnect network and electrically connecting the light-detecting components to the second embedded interconnect network.

In another aspect, the invention provides a method for performing optical analysis using devices of the invention, as described above. In one embodiment, the method includes fluidically self-assembling a plurality of freestanding light-emitting components having a first shape and a plurality of freestanding light-detecting components having a second shape on a template having an embedded interconnect network using component-specific shaped recesses in the template, where the components are connected to the embedded interconnect network by an attachment means; positioning the template such that the light-emitting components and the light-detecting components are in optical communication with an analyte; activating the light-emitting components such that light emitted from the light-emitting component produces an optical response in the analyte; and detecting the optical response with the light-detecting components.

While illustrative embodiments have been illustrated and described, it will be appreciated that various changes can be made therein without departing from the spirit and scope of the invention.

The invention claimed is:

1. A device for optical analysis, comprising:
   a template having a plurality of first recessed binding sites with a first shape and a plurality of second recessed binding sites with a second shape, the template having an embedded interconnect network interconnecting the first and second recessed binding sites, wherein each of the first and second recessed binding sites contains an attachment means;
   a plurality of light-emitting components having the first shape and at least two electrodes, received into at least some of the first recessed binding sites and electrically connected to the embedded interconnect network by the attachment means; and
   a plurality of light-detecting components having the second shape and at least two electrodes, received into at least some of the second recessed binding sites and electrically connected to the embedded interconnect network by the attachment means.

2. The device of claim 1, further comprising a channel adapted to receive a fluid, wherein at least some of the light-emitting components and at least some of the light-detecting components are in optical communication with the channel.

3. The device of claim 1, wherein the attachment means is a solder.

4. The device of claim 1, wherein the light-emitting component electrodes are formed on only one side of the light-emitting components and comprise a circular electrode substantially centered on the light-emitting component and an annular electrode disposed around the circular electrode.

5. The device of claim 1, wherein the light-emitting components are selected from the group consisting of light-emitting diodes, semiconductor lasers, and vertical-cavity surface-emitting lasers.

6. The device of claim 1, wherein the first shape is selected from the group consisting of circular, square, rectangular, triangular, and cruciform.

7. The device of claim 1, wherein the plurality of light-emitting components comprise a first plurality of light-emitting components having a first emission spectrum and a second plurality of light-emitting components having a second emission spectrum, wherein the first emission spectrum and the second emission spectrum are different.

8. The device of claim 1, wherein the plurality of light-detecting components comprise a first plurality of light-sensing components having a first absorption spectrum and a second plurality of light-sensing components having a second absorption spectrum, wherein the first absorption spectrum and the second absorption spectrum are different.

9. The device of claim 1, wherein the light-emitting components and the light-detecting components comprise components in a fluorescence analysis system.

10. A device for optical analysis, comprising:
    a first template having a plurality of first recessed binding sites with a first shape, the first template having a first embedded interconnect network interconnecting the first recessed binding sites, wherein each of the first recessed binding sites contains an attachment means;
    a plurality of light-emitting components having the first shape and at least two electrodes, received into at least some of the first recessed binding sites and electrically connected to the first embedded interconnect network by the attachment means;
    a second template having a plurality of second recessed binding sites with a second shape, the second template having a second embedded interconnect network interconnecting the second recessed binding sites, wherein each of the second recessed binding sites contains an attachment means; and
    a plurality of light-detecting components having the second shape and at least two electrodes, received into at least some of the second recessed binding sites and electrically connected to the second embedded interconnect network by the attachment means.

11. The device of claim 10, further comprising a channel adapted to receive a fluid, wherein at least some of the light-emitting components and at least some of the light-detecting components are in optical communication with the channel.

12. The device of claim 10, wherein the attachment means is a solder.

13. The device of claim 10, wherein the light-emitting component electrodes are formed on only one side of the light-emitting components and comprise a circular electrode substantially centered on the light-emitting component and an annular electrode disposed around the circular electrode.

14. The device of claim 10, wherein the first template and the second template comprise a unitary template.

15. The device of claim 10, wherein the first shape and the second shape are different.

16. The device of claim 10, wherein the first embedded interconnect network and the second embedded interconnect network are connected.

17. The device of claim 10, wherein the light-emitting components are selected from the group consisting of light-emitting diodes, semiconductor lasers, and vertical-cavity surface-emitting lasers.

18. The device of claim 10, wherein the first shape is selected from the group consisting of circular, square, rectangular, triangular, and cruciform.

19. The device of claim 10, wherein the plurality of light-emitting components comprise a first plurality of light-emitting components having a first emission spectrum and a second plurality of light-emitting components having a second emission spectrum, wherein the first emission spectrum and the second emission spectrum are different.

20. The device of claim 10, wherein the plurality of light-detecting components comprise a first plurality of light-sensing components having a first absorption spectrum and a second plurality of light-sensing components having a second absorption spectrum, wherein the first absorption spectrum and the second absorption spectrum are different.

21. The device of claim 10, wherein the device comprises a fluorescence analysis system.

* * * * *